(12) United States Patent
Maruyama et al.

(10) Patent No.: US 6,311,559 B1
(45) Date of Patent: Nov. 6, 2001

(54) VIBRATION MEASUREMENT METHOD AND APPARATUS

(75) Inventors: Tetsuro Maruyama; Akiyoshi Ohno, both of Shizuoka (JP)

(73) Assignee: Suzuki Motor Corporation, Hamamatsu (JP)

( * ) Notice: Subject to any disclaimer, the term of this patent is extended or adjusted under 35 U.S.C. 154(b) by 0 days.

(21) Appl. No.: 09/429,319

(22) Filed: Oct. 28, 1999

(30) Foreign Application Priority Data

Mar. 31, 1998 (JP) .................................................. 10-103736
Oct. 29, 1998 (JP) .................................................. 10-309019

(51) Int. Cl.⁷ .................................................. G01N 29/00
(52) U.S. Cl. .............................. 73/655; 73/649; 73/653; 73/657
(58) Field of Search .............................. 73/655, 649, 652, 73/653, 656, 657, 596; 356/486, 493, 498; 702/56

(56) References Cited

U.S. PATENT DOCUMENTS

| 3,869,904 | * | 3/1975 | Gabor ...................................... 73/67.5 |
| 4,633,715 | * | 1/1987 | Monchalin .............................. 73/657 |
| 4,913,547 | * | 4/1990 | Moran et al. .......................... 356/349 |
| 5,146,776 | * | 9/1992 | Twerdochlib et al. ................. 73/1.85 |
| 5,394,233 | * | 2/1995 | Wang .................................. 356/5.01 |
| 5,841,030 | * | 11/1998 | Honsberg et al. ..................... 73/579 |
| 5,900,935 | * | 5/1999 | Klein et al. .......................... 356/347 |

FOREIGN PATENT DOCUMENTS 7-167956   7/1995   (JP) .

* cited by examiner

Primary Examiner—Daniel S. Larkin
Assistant Examiner—Jacques Saint-Surin
(74) Attorney, Agent, or Firm—McGinn & Gibb, PLLC

(57) ABSTRACT

The present invention discloses a vibration measurement method and apparatus using a self-mixing type laser Doppler vibration meter. The vibration measurement method according to the present invention comprises: an inclination value calculation step S3 for calculating an ascending inclination and a descending inclination for each beat wave; and a turning point identification step S4 for identifying the turning point of a vibrating object according to the inclination change along the time axis.

19 Claims, 16 Drawing Sheets

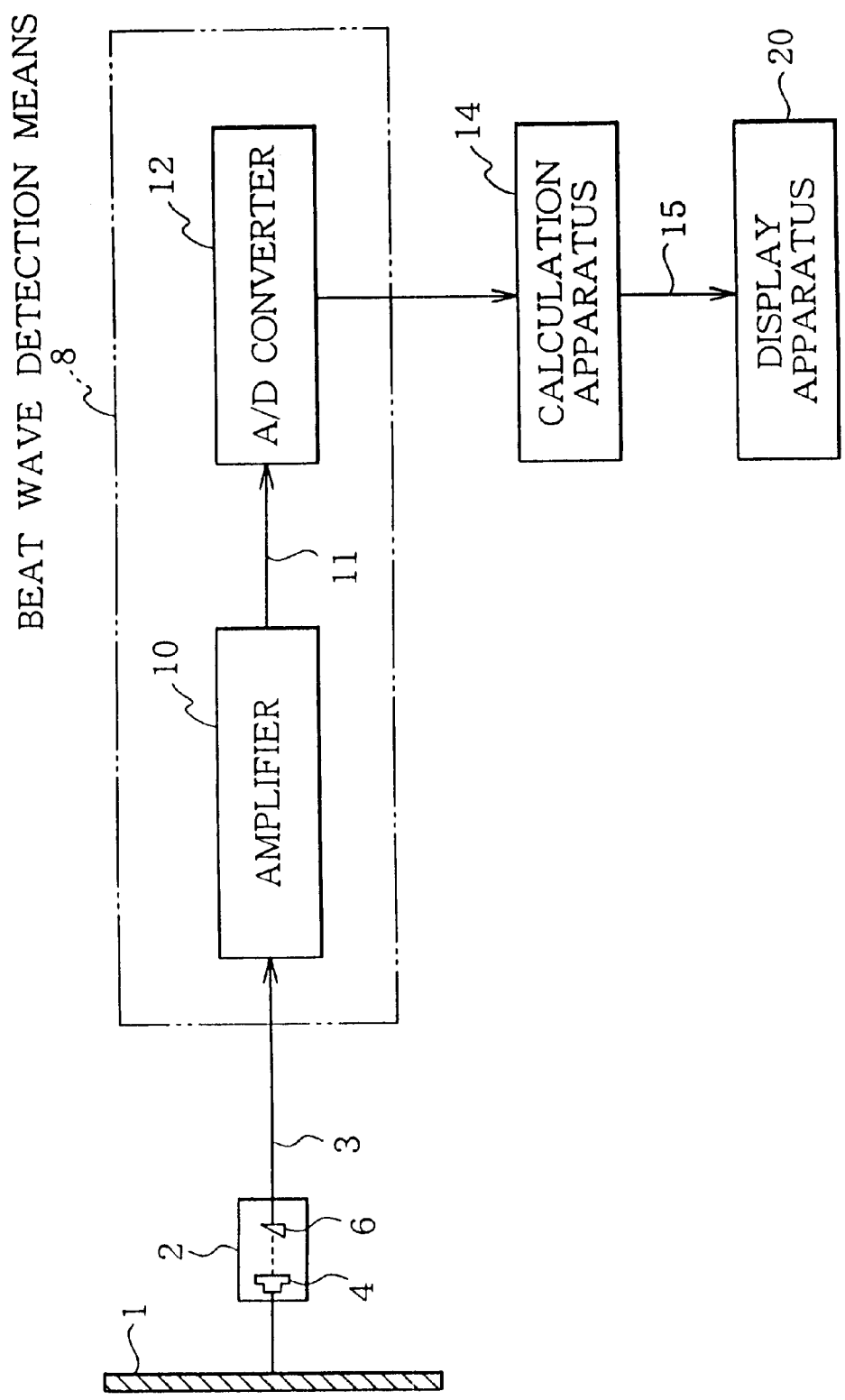

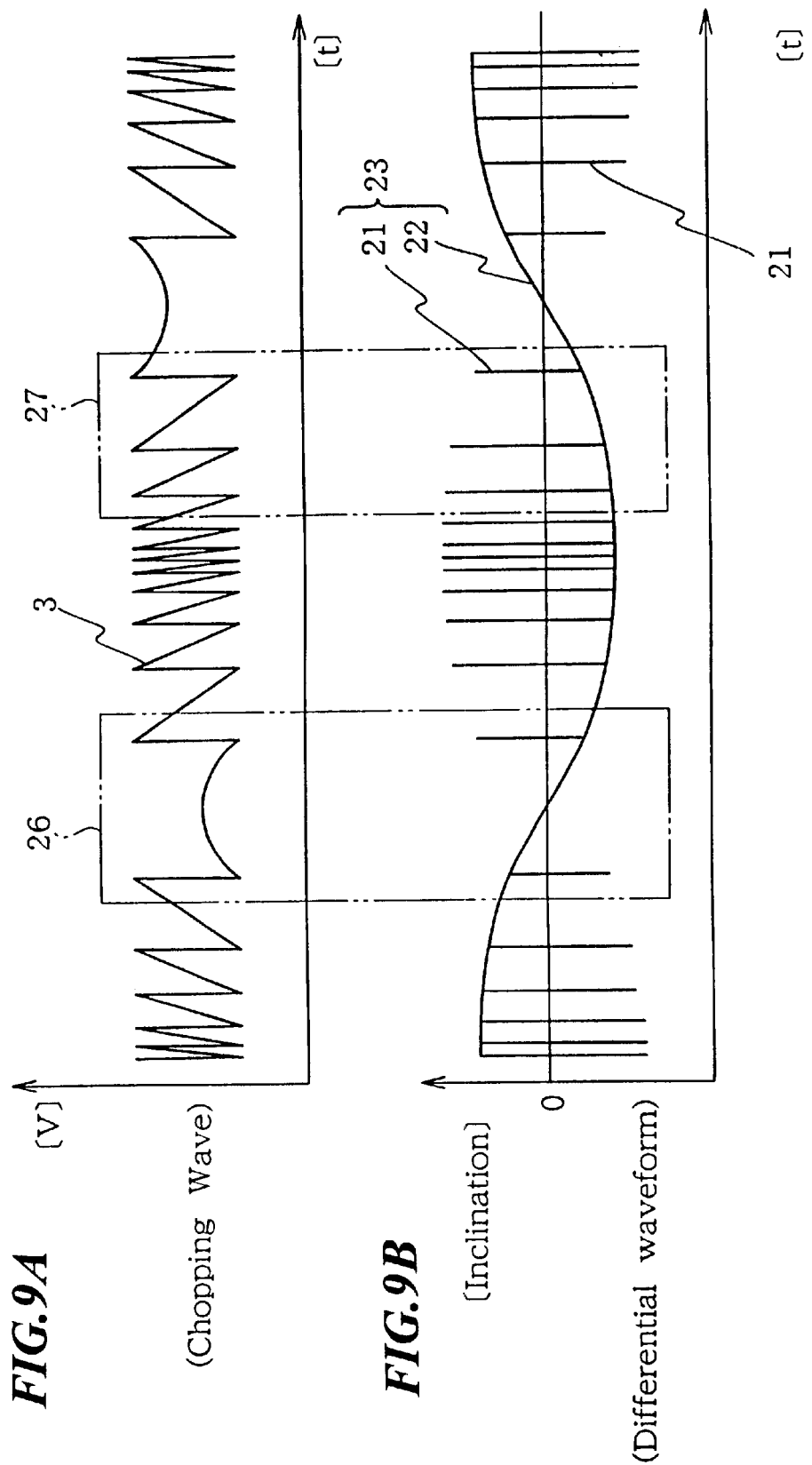
FIG.9A (Chopping Wave)
FIG.9B (Differential waveform)

VIBRATION MEASUREMENT METHOD AND APPARATUS

BACKGROUND OF THE INVENTION

1. Field of the Invention

The present invention relates to a vibration measurement apparatus and a recording medium containing a vibration measurement program and in particular, to a vibration measurement apparatus of non contact type calculating a displacement of an object utilizing the Doppler effect of the laser beam and a recording medium containing such a vibration measurement program.

This vibration measurement apparatus can be applied to various experiment analyses of the automobile production technology or the like. More specifically, engine vibration analysis, body vibration, analysis of noise within an automobile, muffler vibration analysis, and the like. Since the vibration measurement apparatus is non-contact type and capable of accurately measuring vibration in a very small area, it can be applied to inspection in semiconductor production as well as inspection of a drill and other instruments. Furthermore, the vibration measurement apparatus can be used for detecting can be applied for detecting abnormal vibration in a production plant using a motor as well as leak from the water pipe and gas pipe. Furthermore, the vibration measurement apparatus can be employed for checking sweetness of watermelon other big fruits by knocking on the fruits to generate a sound. Here, an "object to be measured" includes a vast range from engines to watermelons.

2. Description of the Related Art

Conventionally, a speed indicator utilizing the laser beam Doppler effect has been used. The laser beam Doppler effect can also be used for measuring a displacement of an object to be measured as follows. That is, an oscillated laser beam is mixed with a reflected beam in a laser resonator. As a result, a beat wave of the laser beam can be detected by a photo detector (photodiode and the like). Here, if the object has moved a certain distance (half of the laser beam wavelength $\lambda$), a chopping wave appears. Accordingly, by counting the number of the chopping waves, it is possible to calculate the displacement of the object.

However, a displacement smaller than the certain distance of one chopping wave cannot be accurately measured. Especially, when the object is vibrating, it is difficult to detect a turning point. That is, displacing object moves to the maximum point by vibration and then displacement becomes zero. After this, the object starts to displace in the opposite direction. Here, the chopping wave has a gentle slope and it becomes difficult to detect the turning point, i.e., the moment when the vibration direction has changed.

To cope with this, there is a method to calculate the turning point according to the highest speed position in on vibration cycle. The highest speed position can be detected in a comparatively stable state. However, if the object vibrates with a plurality of frequency components, a displacement in one direction is not symmetrical to a displacement in the other direction. This disables to calculate a turning point according to the highest speed position in one vibration cycle.

The vibration measurement apparatus utilizing the Doppler effect of the laser beam intends to perform in non-contact state the function of the acceleration pickup to be fixed on the object to be measured. Accordingly, it is desired to preferably measure the vibration characteristics of the object to be measured. However, If the turning point cannot be calculated or detected accurately, a displacement amount is added without turning. Thus, it is impossible to calculate with a high accuracy.

Moreover, when the vibrating plane contains a displacement of large highest speed and a small highest speed, a plurality of waves are overlapped and it is impossible to calculate a turning point for the small highest speed. Furthermore, it is difficult to identify a turning point of vibration which has once slowed down speed and then increases the speed in the same direction.

SUMMARY OF THE INVENTION

It is therefore an object of the present invention to provide a non-contact type vibration method and apparatus capable of accurately calculating the vibration turning point.

Another object of the present invention is to preferably calculate a vibration turning point even if a plurality of vibrations are overlapped in the object to be measure.

Still another object of the present invention to identify a turning point even if the vibration plane moving speed has slowed down and then increases the moving speed in the same direction.

In the present invention, utilizing the general vibration characteristics and the relationships between a beat wave chopping wave and a displacement amount of the object to be measured, a turning point of the object to be measured is decided according to a continuous change of the chopping wave. When identifying a turning point according to a chopping waveform, there is an approach using differential and an approach using integral.

The differential approach identifies a turning point according to a continuous inclination change of the chopping wave in a beat wave. This differential approach also utilizes a relationship between the object displacement direction and the beat wave inclination.

The integral approach identifies a turning point according to a continuous change of the chopping wave area or wavelength. In this approach, a turning point is identified when the object speed is slowed down and then increases speed.

The differential approach extracts a change of displacement direction.

Firstly, the differential approach will be detailed. In a beat wave, a chopping wave has ascending portion and a descending portion, one of which has inclination almost 90 degrees and the other has a gentle slope. This gentle slope may be an ascending portion or a descending portion according to the movement direction of the object to be measured. The inclination itself is determined by the displacement speed of the vibrating plane. When the vibrating plane is coming nearer to the vibration measurement apparatus, the gentle slope is ascending; and when the vibrating plane is going away from the vibration measurement apparatus, the gentle slope is descending.

The chopping wave inclination changes according to the displacement speed but no change can be seen in the gentle slope. If the gentle slope is ascending, the inclination sign is plus and if the gentle slope is descending, the inclination sign is minus. When the vibrating plane displacement changes its direction, the ascending portion or descending portion having a gentle slope is reversed and the sign is reversed. According to the present invention, a turning point is identified before and after the sign is changed.

More specifically, the present invention includes steps of: applying a laser beam oscillated in a laser resonator, to an object to be measured; photo detecting the return laser beam; photo-electrically converting the mixture the return beam with the oscillated laser beam; and a signal processing for analyzing a waveform of the beat wave output from the photo-electrical conversion.

The signal processing step includes: an inclination calculating step for calculating the ascending inclination and a descending inclination of each beat wave; and identification of a turning point of the object to be measured, according to the inclination value changes along the time axis.

The inclination calculation step calculates an ascending inclination and a descending inclination. Then, it can be known which of the inclination is more gentle. The return point identification step identifies a return point of the object to be measured, according to the inclination value change along the time axis. Thus, the turning point is identified depending whether the gentle slope is ascending or descending. Accordingly, the direction change can be detected regardless of the vibrating plane moving speed. This assures to detect a turning point of the vibration even if the object to be measured exhibits a complicated vibration such as speed change in the middle.

The data on this beat wave inclination can be handled through a differential waveform of the beat wave. For the interval excluding the position of the turning point, the beat wave inclination is as follows. That is ascending gentle slopes alternate with descending steep slopes or ascending steep slopes alternate with descending gentle slopes. This relationship is maintained until a turning point occurs to change the advance direction. Since ascending or descending steep slopes are completed in a short time, if the beat wave is differentiated, a needle-shaped peak is generated for each one beat wave. The peak of the differentiated waveform will be referred to as a needle peak in this Specification. The differentiated waveform excluding the needle peaks correspond ascending or descending gentle slopes. The base waveform excluding the needle peaks will be referred to as a slope waveform.

When a beat wave having a rounded portion is differentiated, the slop waveform becomes gentle. If the beat wave is rectified by connecting a peak and bottom with a straight line before differentiation, the slope waveform is changed in stepped manner for each of the beat wave piece. The angle of this slope waveform may be in a range from zero to 90 degrees or in a range from 90 to 180 degrees according to the object displacement direction. When the beat wave is below 90 degrees, the sign is plus, and when the beat wave exceeds 90 degrees, the sign is minus. Accordingly, where the slop waveform sign is reversed, vibrating plane displacement direction is change. The present invention utilizes this phenomenon and identifies a turning point without depending on the vibrating plane speed.

Moreover, the isolation of needle peaks from the slop waveform portion may depend on the zero cross duration of the differentiated wave.

Next, explanation will be given on the integral approach. There is a method to use a wavelength as a characteristic amount. The apparatus calculating a vibration based on the wavelength includes: a photo detection unit for observing the laser beam reflected from the object to be measured; a signal processing unit for analyzing the waveform signal output from this photo detection unit, and detecting the beat wave; and a calculation a displacement amount of the object to be detected, according to the beat wave state detected by the signal processing unit. Furthermore, the calculation unit includes: a wavelength calculation unit for calculating each beat wave piece; and a turning point identification unit for extracting a wave piece having a long wavelength from a plurality of waveforms calculated by the wavelength calculation unit, and identifying a turning point of the object displacement direction. Here, the beat wave is a signal changing according to the speed of the object surface and normally, is a chopping wave. Moreover, the beat wave includes a chopping wave broken at the turning point of the vibration. Furthermore, the term "chopping wave" may be used in the same meaning of the beat wave. Especially, the chopping wave wavelength means wavelength of each waveform piece.

According to the present invention, the wavelength calculation unit calculates a wavelength of each chopping wave piece and extracts a waveform of having a long wavelength from a plurality of wave pieces. The wave piece having a long wavelength appears when the object to be measured moves very slowly or has stopped. Accordingly, a turning point can be extracted by catching a long wavelength wave piece regardless of the oscillation cycle of the object to be measured. Even if the vibration of the object to be measured contains a plurality of frequency components, it is possible to preferably identify the turning point. Thus, the vibration of the object to be measured can be measured with a non-contact method.

The turning point identification according to a waveform having the longest wavelength is performed as follows for example. A center value of the set of waveforms having a wavelength exceeding a threshold value is identified as the turning point. Moreover, among waveforms having a wavelength difference is zero-crossed, a position of a wave having a wavelength exceeding a threshold value is identified as a turning point.

BRIEF DESCRIPTION OF THE DRAWINGS

FIG. 2 explains signals used in the processes of FIG. 1.

FIG. 3 is a block diagram showing a configuration of a vibration measurement apparatus used in the method of FIG. 1.

FIG. 6 shows signals used in the processes of FIG. 5.

FIG. 7 shows examples of rectification of the beat wave.

FIG. 9 shows waveforms indicating signals used in the processes shown in FIG. 8. FIG. 9A is an example of beat, (chopping) wave; and FIG. 9B shows an example of differential waveform of the beat (chopping) wave.

FIG. 10 is an enlarged view of FIG. 9.

DESCRIPTION OF THE PREFERRED EMBODIMENTS

<Embodiment 1>

Figure 1:
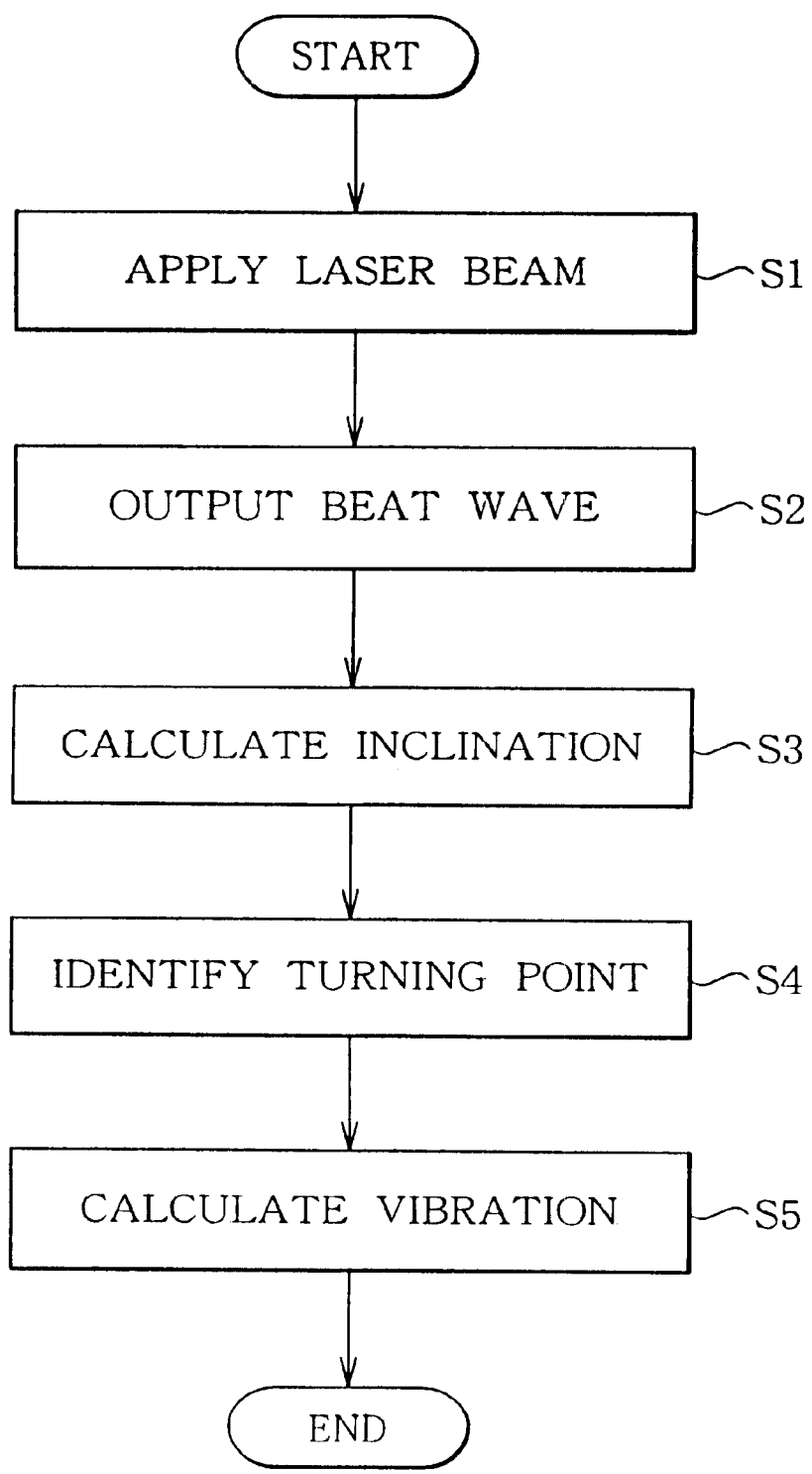
FIG. 1 is a flowchart showing a configuration of the first embodiment of the present invention.

FIG. 1 is a flowchart showing a configuration of a vibration measurement method according to the present invention. This vibration measurement method includes: laser beam application step S1 for applying a laser beam oscillated by a laser resonator, to an object to be measured; a photo-electric conversion step (S2) for receiving a return laser beam and photo-electrically converting the laser beam mixture of the received laser beam with a laser beam oscillated in the laser resonator; and a signal processing step for analyzing a waveform state of the beat wave output from the step S2. The signal processing step includes: inclination calculation step S3 for calculating an inclination while a beat wave is ascending and an inclination while the beat wave is descending; and turning point identification step S4 for identifying the turning point of an object to be measured, according to the change of the inclinations during ascending and during descending along the time axis.

FIG. 2 shows an example of signal which is input and output in the steps of FIG. 1. As shown in FIG. 2A, a displacement 1a having a slow down portion in the middle of the displacement can be shown as a beat wave 3 in FIG. 2B. In FIG. 2A, the laser resonator is located above the wave. As shown in FIG. 2, when the vibration plane of the object to be measured approaches the laser resonator, the beat wave ascending inclination becomes gentle and when the object to be measured goes away from the laser resonator, the beat wave descending inclination becomes gentle. This is because the phase of the Doppler frequency is changed depending on the displacement direction of the object to be measured. In this embodiment, in the inclination calculation step, inclination values shown in FIG. 2C, for example, are extracted. In the case of FIG. 2B, a chopping wave piece 32 has an ascending portion 30 and a descending portion 31 and the one having inclination with a smaller absolute value remains. When an ascending portion and a descending portion have almost identical absolute value of inclination, such as the portion 33 in FIG. 2C remains as it is.

Figure 2A:
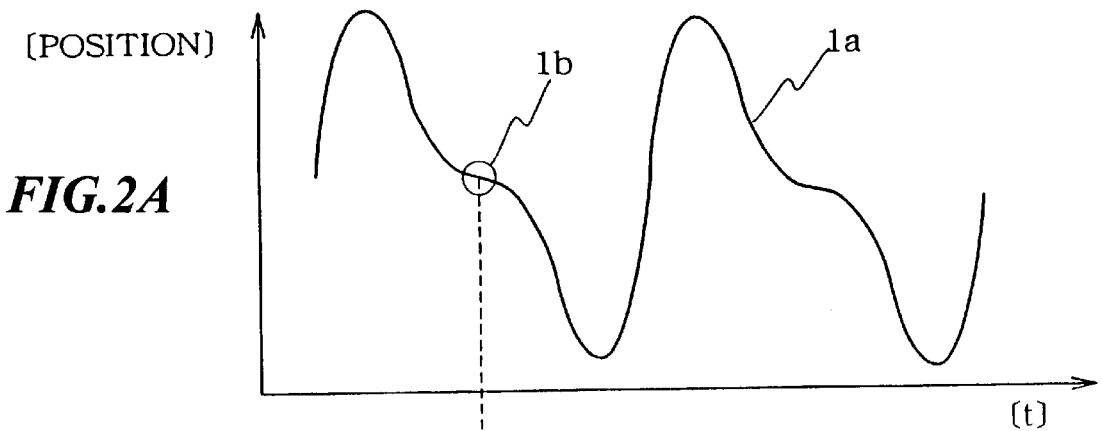
FIG. 2A shows a vibration displacement along the time axis.
Figure 2B:
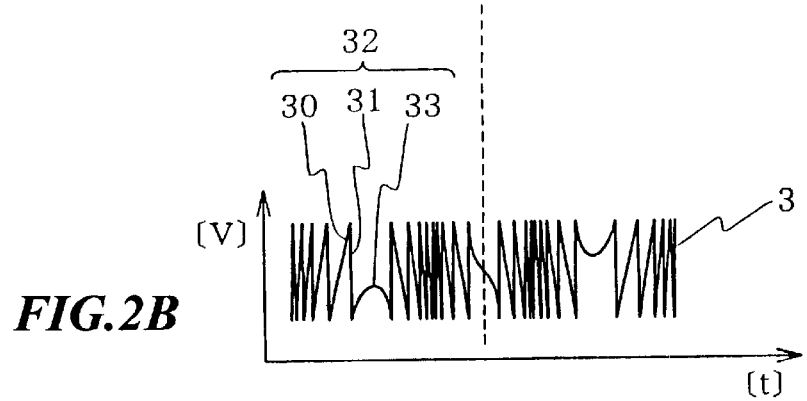
FIG. 2B is an example of beat wave corresponding to this displacement.
Figure 2C:
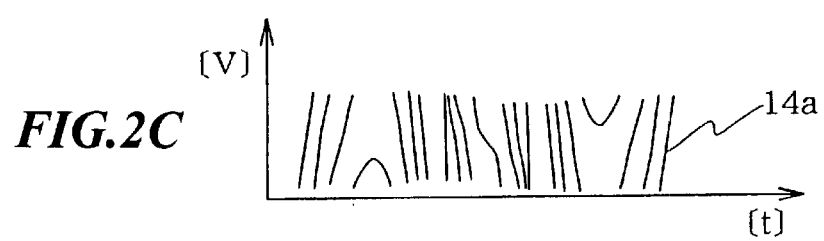
FIG. 2C is an example of extraction of inclinations of the beat wave.
Figure 2D:
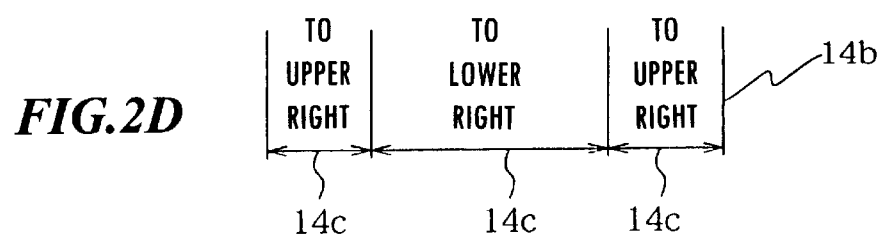
FIG. 2D is an example of inclination features extracted.

For data 14a on the inclination value change along the time axis is further used to generate a data 14b shown in FIG. 2D. In the turning point identification step S4, the inclination change point shown in FIG. 2D is identified as a turning point. Accordingly, there is no danger of identifying the slow down portion 1b as a turning point. When a turning point is identified, a turning waveform is generated so as to be high or low at the turning point and the vibration cycle of the object to be measured can be known. Moreover, since the chopping wave is generated when the vibrating plane has displaced $\lambda/2$, it is possible to create an object displacement data by counting the chopping waves and reversing the displacement direction at the turning point.

FIG. 3 shows a hardware configuration of a vibration measurement apparatus which can be preferably used for the vibration measurement method of the present embodiment. The vibration measurement apparatus includes: photo-detector unit 2 for observing a laser beam reflected from an object 1 to be measured; a beat wave detection unit 8 for analyzing the waveform signal output from the photo-detection unit 2 and detecting a beat wave; a calculation apparatus for analyzing the beat wave detected by the beat wave detection unit 8; a display apparatus for displaying the vibration data calculated by the calculation unit.

In the example of FIG. 3, the calculation apparatus 14 functions as an inclination value calculation unit and as a turning point identification unit. The calculation apparatus may be a work station, micro processor, or a personal computer including a main storage and a CPU. When a program for calculating the turning point is executed in this CPU, the calculation apparatus 14 functions as an identification unit. Moreover, it is also possible to use a logical circuit or analog circuit instead of the calculation apparatus 14.

Figure 4:
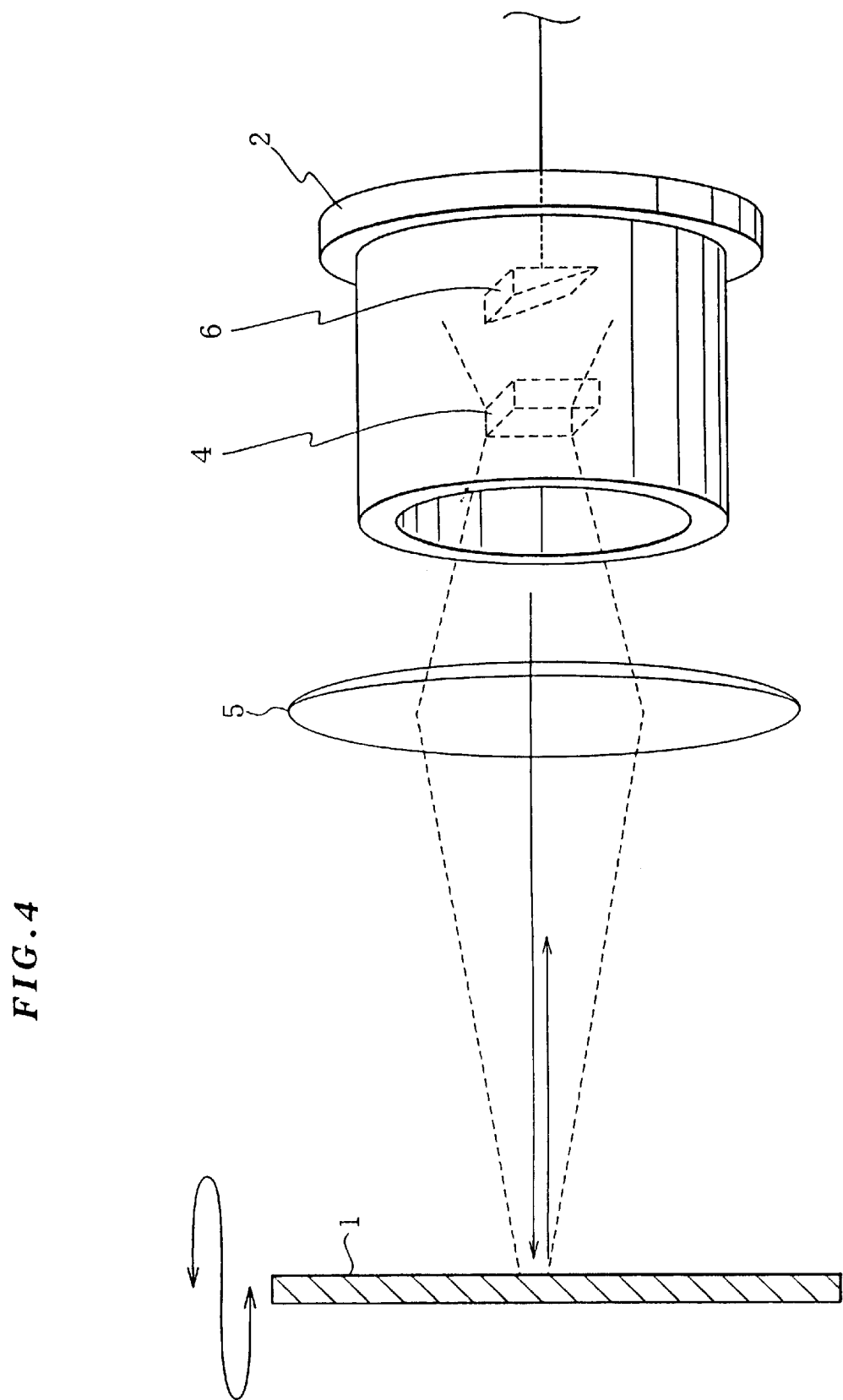
FIG. 4 is a perspective view of a photo detecting unit shown in FIG. 3.

FIG. 4 shows a configuration of the photo-detection unit 2 shown in FIG. 3. The photo-detection unit 2 includes: a laser diode 4 for emitting a laser beam; and a photo diode for receiving the mixture of the oscillated beam in the resonator of the laser diode 4 with a return beam. The laser beam oscillated by the resonator 4 of the laser diode is focused by a lens 5 and applied to the object to be measured.

EXAMPLE 1

Figure 5:
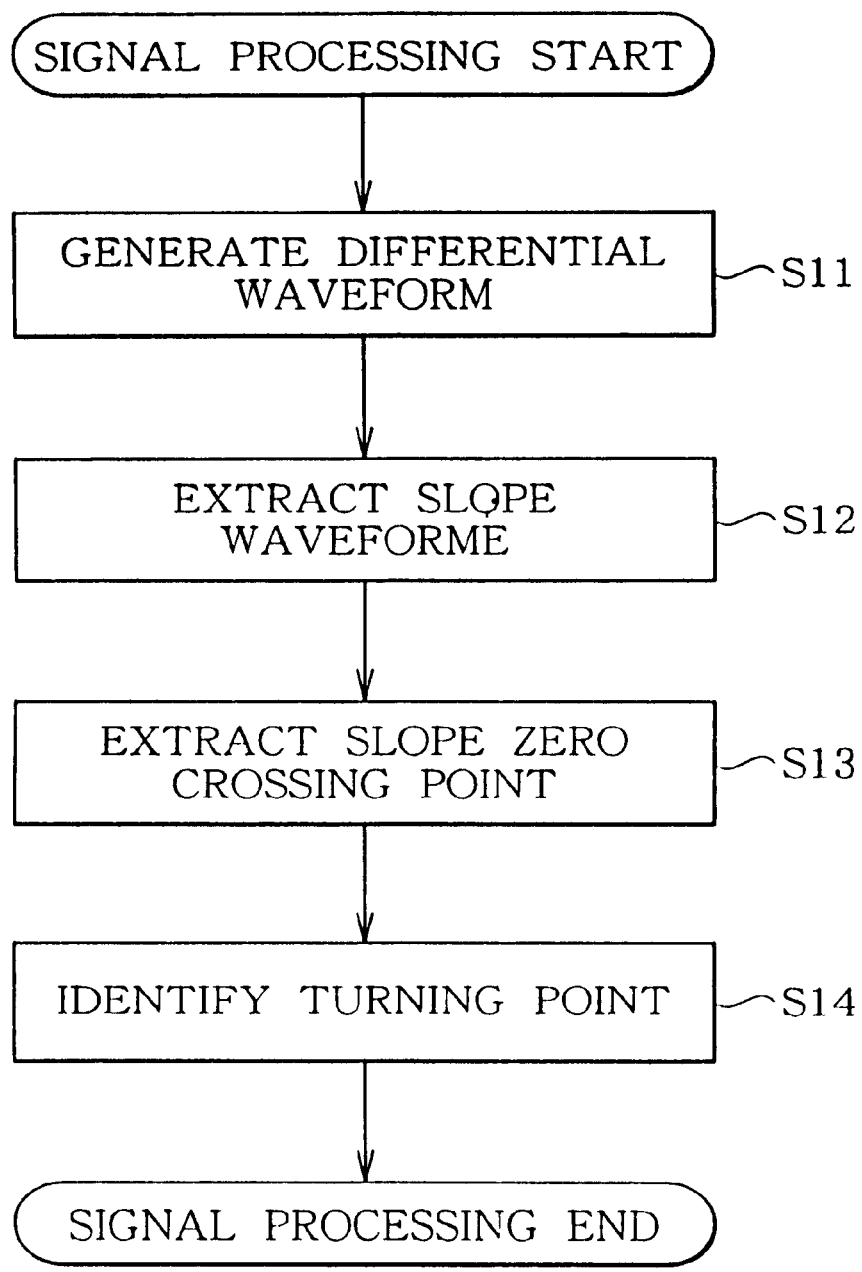
FIG. 5 is a flowchart showing a configuration of Example 1 of the first embodiment.
Figure 6A:
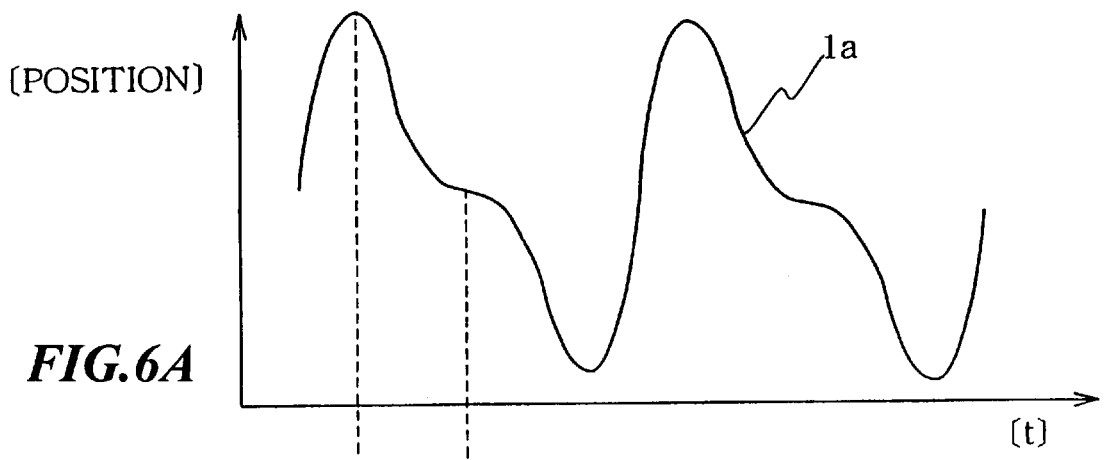
FIG. 6A shows an example of vibration displacement along the time axis.
Figure 6B:
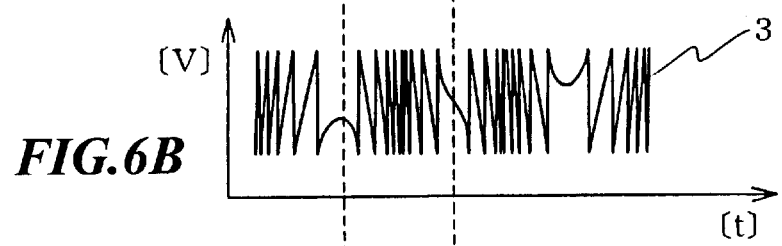
FIG. 6B shows an example of beat wave corresponding to this displacement.
Figure 6C:
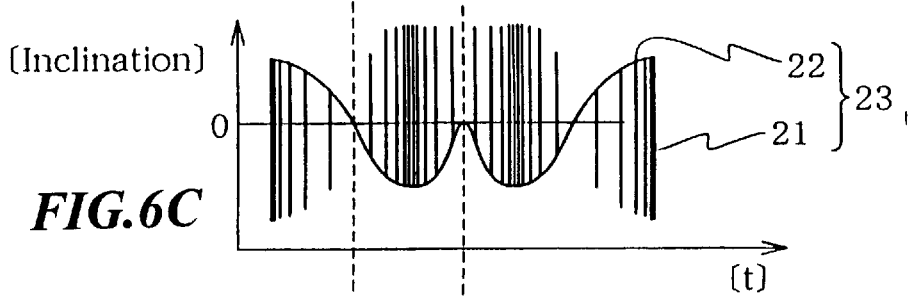
FIG. 6C shows an example of differential waveform of the beat wave.
Figure 6D:
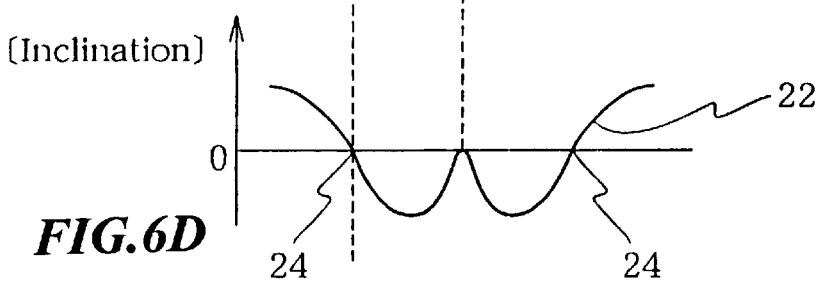
FIG. 6D shows a slope portion extracted from the differential waveform.

Next, an explanation will be given on an example of the present invention. FIG. 5 is a flowchart showing a configuration of the vibration measurement method according to the present invention. Here, the beat wave output step (step S2) is followed by: a differential waveform generation step S11 for generating a differentiated waveform 23 of the beat wave; a slope waveform value extraction step (step S12) for extracting from the differentiated waveform a differential value (divided difference) of the slope waveform 22 serving as a base of needle peaks 11 which zero crosses twice in a short period of time; a slope zero cross point extraction step (step S13) for detecting in the differentiated value of the slope waveform 22, a slope zero cross point 24 which zero crosses in a longer period of time than the aforementioned short period of time; and a turning point identification step (step S14) for deciding that a turning point of the object to be measured is in the vicinity of the zero cross point 24 of the slop waveform 22 which has been extracted in the slope zero cross point extraction step S13.

FIG. 6 shows an example of signal used in the steps of FIG. 5. The beat wave shown in FIG. 6 becomes as shown in FIG. 6C when differentiated. The differentiated waveform 23 contains needle peaks 21 corresponding to a steep slope of ascending or descending portion and a slope waveform 22 as the base of the needle peak 21. The slope waveform 22 corresponds to a gentle slope of ascending or descending portion. FIG. 6B shows a differentiated waveform of a beat wave having a rounded portion instead of the beat wave constituted by straight lines like FIG. 7C. The differential waveform may be generated by calculating a digital data difference change or by using a high band passing CR circuit. Any method can be employed if the inclination change can be obtained.

In the example of FIG. 5, the zero cross point 24 is extracted where the slope waveform value is 0. The turning point identification step S14 decides that the turning has occurred in the vicinity of the zero cross point 24. Thus, the turning point can be accurately detected regardless of the vibrating plane displacement speed change.

Figure 7A:
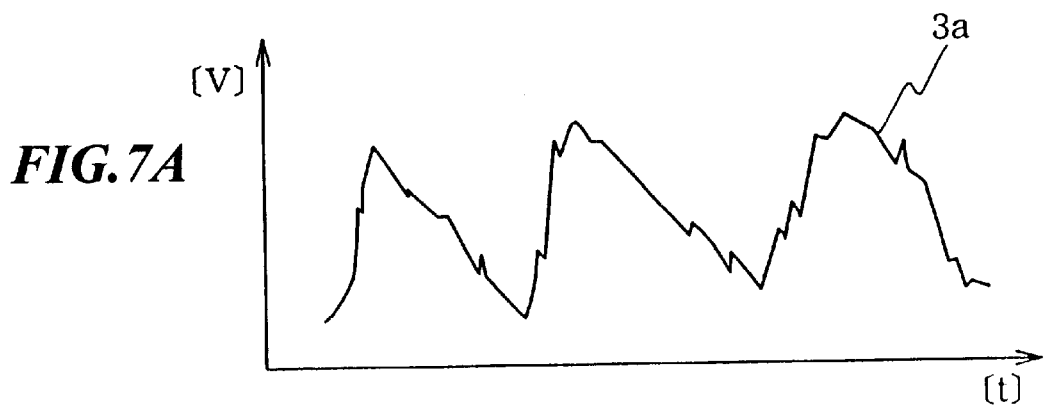
FIG. 7A shows an example of beat waveform overlapped by a high frequency component.
Figure 7B:
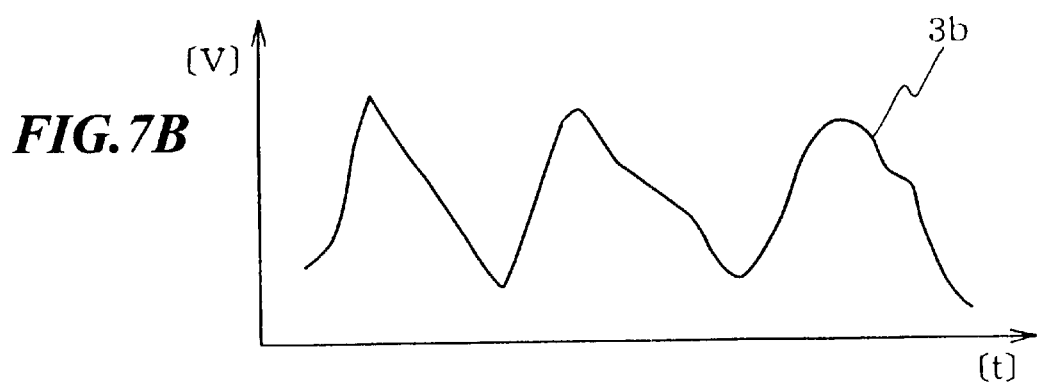
FIG. 7B shows this beat wave which has been smoothed.
Figure 7C:
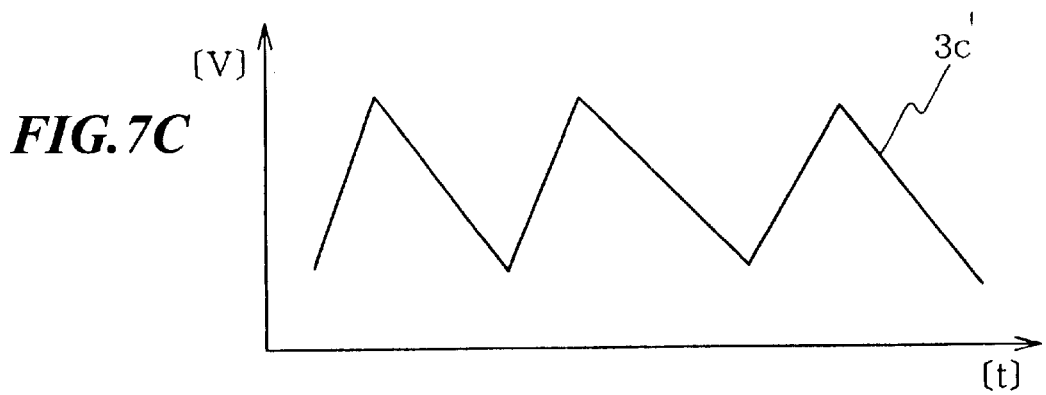
FIG. 7C the smoothed beat wave which has been further rectified so as to have a differential value 0.

FIG. 7 shows waveforms for explaining a beat waveform rectification using a differentiated waveform for isolating the chopping wave component from noise in a single wavelength calculation process. In the photo-detecting unit 2 shown in FIG. 4, the beat wave may be overlapped by a high frequency component depending on the measurement environment. If the beat wave 3a in FIG. 7A is smoothed, the waveform shown in FIG. 7B is obtained. The smoothed beat wave 3b is further differentiated and the points having differential value zero are connected to one another. Then the waveform is rectified as shown in FIG. 7C. The rectified beat wave 3c facilitates counting of chopping waves.

Moreover, a smoothed and differentiated waveform can be used not only for the beat wave rectification shown in FIG. 7 but also for turning point calculation shown in FIG. 6. The differentiated waveform to be used for waveform rectification can also be used as the differentiated waveform shown in FIG. 6C. This reduces the time required for a turning point identification.

EXAMPLE 2

Figure 8:
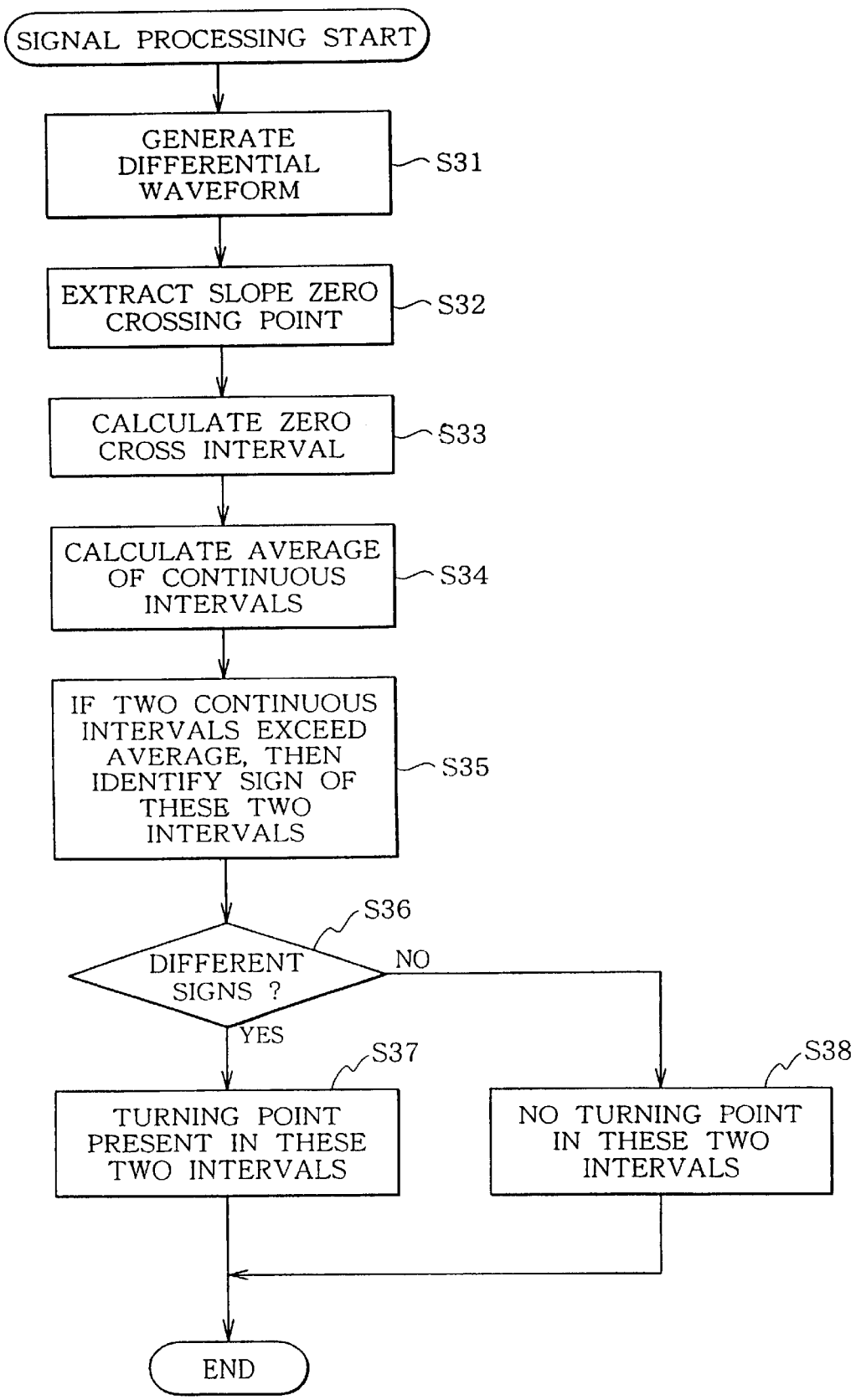
FIG. 8 is a flowchart showing configuration of Example 2 of the first embodiment.

FIG. 8 is another flowchart showing a configuration of another example of the present invention.

In the example of FIG. 8, the beat wave output step S2 of FIG. 1 is followed by: differential waveform generation step (step S31) for generating a differential waveform 23 about the beat wave 3; zero cross point extraction step (step S32) for extracting a zero cross point 23 where the differential waveform 23 generated in step S32 zero crosses; a zero cross interval calculation step (step S33) for calculating intervals 24a and 24b from a zero cross point 23 to the next cycle zero cross point 23; an average interval length calculation step (step S34) for calculating an average of three zero cross intervals calculated in the zero cross interval calculation step S33; differential sign identification step (step S35) for identifying the sign of the two continuous intervals 24b exceeding the average; deciding whether the two continuous intervals have different signs (step S36); and a turning point identification step consisting of two cases: in a case that the two continuous interval have different signs, it is decided that a turning point is present in the two continuous interval (step S37); and in a case that the two continuous interval have an identical sign, it is decided that no turning point is contained (step 38).

FIG. 9 and FIG. 10 show a waveform example used in the processing of FIG. 8. FIG. 9A shows a beat wave (chopping wave) is differentiated into the waveform of FIG. 9B. Similarly as in FIG. 2B, the differential waveform 23 contains a needle peak 21 and a slope 22. In the example of FIG. 5, a slope waveform is extracted in step S12. However, this time, zero cross points are extracted from the needle peak 21 and the slope waveform.

Figure 10A:
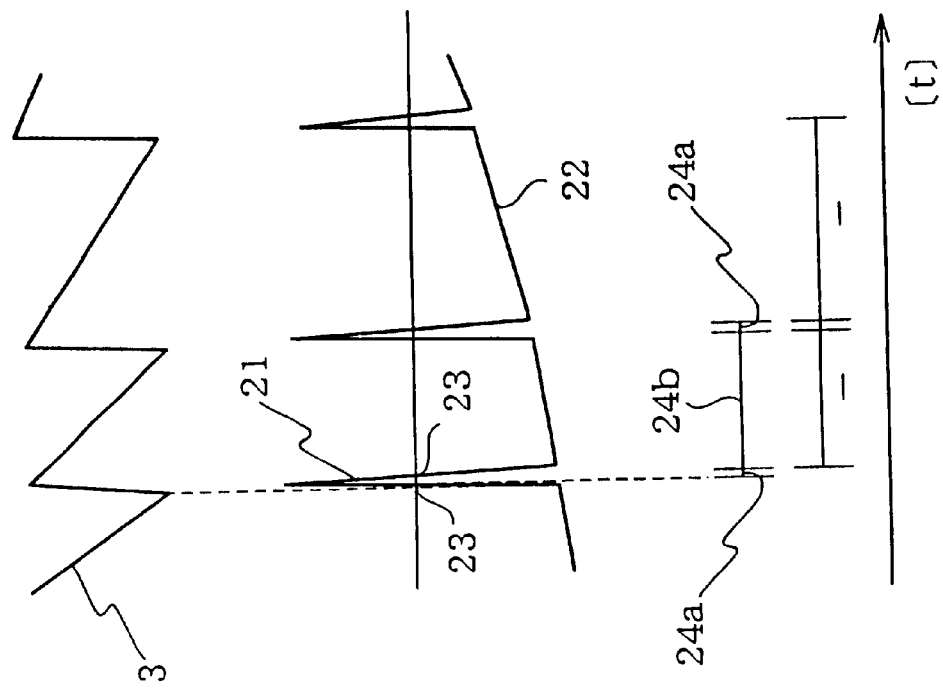
FIG. 10A corresponds to the portion 26 in FIG. 9.
Figure 10B:
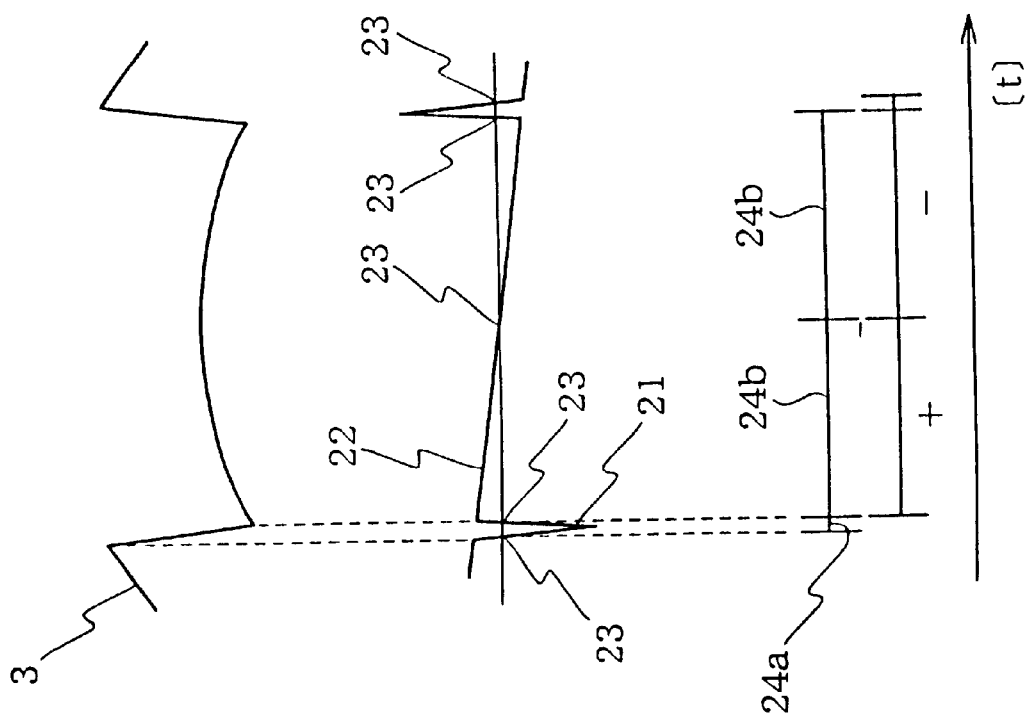
FIG. 10B corresponds to the portion 27 in FIG. 9.

FIG. 10A shows the portion 26 of FIG. 9 as a chopping wave and a differentiated waveform. FIG. 10B shows the portion 27 of FIG. 9 as a chopping wave and a differentiated waveform. As shown in FIG. 10, the needle peak 21 has an interval 24a between the a first zero cross points 23 and a second zero cross point 23. This interval 24a is comparatively short. In contrast to this, an interval 24b between the second zero cross point 23 of the needle peak and the next zero cross point 23 is comparatively long. Accordingly, by calculating an average of the continuous three intervals, it is possible to identify the interval of the needle peak. That is, in the example of FIG. 10A where the slope waveform 22 zero crosses, in the continuous three intervals, the interval longer than the average is the slope waveform 22.

Among the continuous three intervals, the two intervals 24b of the slope waveform have differentiated values of different signs (plus and minus) as shown in FIG. 10A, or as shown in FIG. 10B, identical signs. The slope waveform has different signs when the slope waveform zero crosses. As has been described above, the slope waveform zero crosses when the displacement direction of the object to be measured is changed. Accordingly, in the three continuous intervals, if two longer intervals than the average interval have different signs of the differentiated waveform, it can be decided that the turning point is between the two intervals.

The method shown in FIG. 8 can be realized by using the vibration measurement apparatus shown in FIG. 3. In this case, the calculation apparatus shown in FIG. 3 includes: a differential processing unit for generating a differentiated waveform of a beat wave; a zero cross point extraction unit for extracting a zero cross point where the differentiated waveform zero-crosses; a zero cross interval calculation unit for calculating an interval from the zero cross point and the next zero cross point; a differential sign identification unit for calculating an average of three continuous intervals and identifying signs of the two continuous intervals longer than the average; a turning point identification unit for deciding that a turning point is present in the two intervals identified in the differential sign identification unit if the two intervals have different signs, and that no turning is present if the two intervals have identical signs.

As has been described above, according to the Example 2, in the case of the waveform of FIG. 6 where the vibrating plane displacement is slowed down in the middle or in the case of a rectangular wave overlapped by a sinusoidal wave, it is possible to obtain vibration displacement for each of the chopping waves, so that the displacement is plotted. When rectifying a beat wave according to the differentiated waveform, by utilizing a differentiated waveform already known at the turning point calculation step, it is possible to rapidly calculate the vibration displacement. Moreover, according to Example 2, it is possible to increase the turning point calculation accuracy while maintaining the vibration displacement measurement accuracy.

<Embodiment 2>

In the second embodiment, an integral approach is taken for identifying characteristics of a chopping waveform. For example, integral approach uses the wavelength of a chopping wave. In this case, a turning point is calculated according to a continuous wavelength change.

Figure 11:
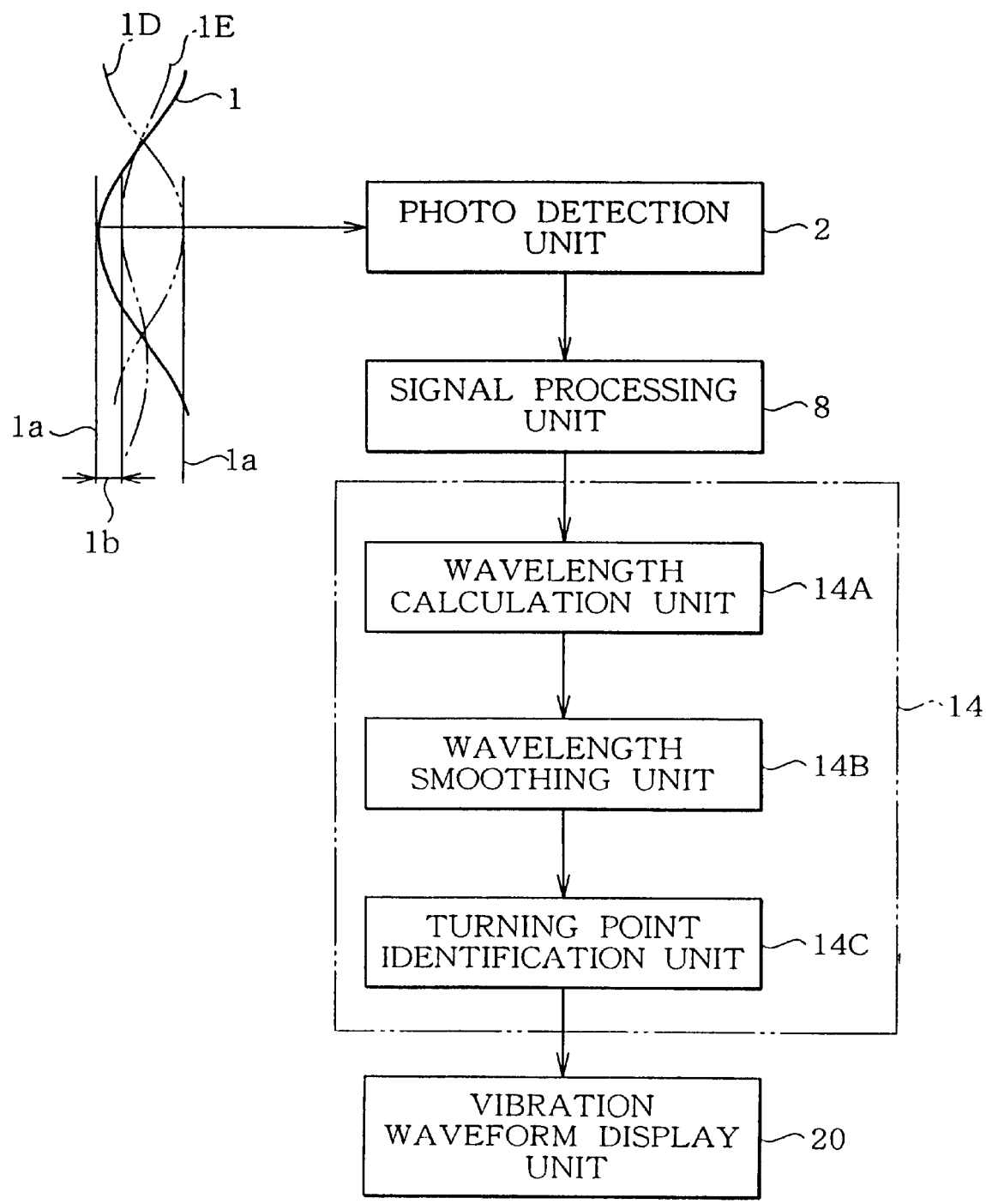
FIG. 11 is a block diagram showing a configuration of a second embodiment of the present invention.

FIG. 11 is a block diagram of a vibration measurement apparatus according to the second embodiment. The vibration measurement apparatus includes a photo detection unit 2 for observing a self-mixed oscillated beam with a reflected beam from an object to be measured; a signal processing unit 8 (beat wave detection unit) for analyzing a waveform signal output from the photo detection unit and detecting a chopping wave (beat wave); and a calculation unit 6 for calculating a displacement amount of the object to be measured, according to the beat wave state detected by the signal processing unit 8.

The calculation unit 6 includes a wavelength calculation unit 14A for calculating a wavelength of each beat wave and a turning point identification unit 14C for extracting the longest wavelength from the plurality of waves calculated by the wavelength calculation unit and identifying the turning point of the object displacement according to position of the wave having the longest wavelength.

Moreover, depending on the sampling frequency when converting a measurement environment and a beat wave into a digital data, the calculation unit preferably includes a wavelength smoothing unit 14B for smoothing wavelength values calculated by the wavelength calculation unit. Thus, when calculating a wavelength of a beat wave, even if a high frequency component added to the beat wave is erroneously detected, the affect of this error is reduced by performing smoothing.

Furthermore, the calculation unit 6 plots a vibration data of the object to be measured according to the turning information (displacement direction data) determined by the turning point identification unit 14C and the number of beat waves. This vibration data is displayed on the display unit 14. Moreover, it is possible to output the vibration data to a vibration analyzing apparatus instead of displaying on the display apparatus.

The photo detection unit 2 mix in a resonator the beam reflected from the vibrating object 1 and receives the mixture and performing photoelectric conversion to the mixture for output to the signal processing unit 8. In order to measure a vibration, firstly, the object 1 to be measured is vibrated. Then, the object starts vibration. As shown in FIG. 11, a measurement plane of the object displaces from an initial position through the position indicated by the alternate long and two short dashes line and slows down displacement near the turning point 1a, and the vibrating plane 1 stops at one of the positions indicated by a symbol 1a. Here, the displacement direction is turned, and the speed is accelerated toward the center of vibration. After that, the speed is again slows down and stops at the other turning point 1a.

As has been described above, in the self-mixing type laser Doppler vibration measurement apparatus, a chopping wave is generated when the object to be measured displaces by a half of the laser beam wavelength $\lambda$, (i.e., $\lambda/2$). When the object displaces rapidly, the inclination of the chopping wave becomes steep and the wavelength becomes shorter. On the other hand, when the object displaces slowly, the inclination of the chopping wave becomes gentle and the wavelength becomes longer. Since the vibration is periodic, the chopping wave obtained by the reflected beam also becomes periodic. More specifically, when the object is in the vicinity of the turning point, the object displaces slowly and the chopping wave has a longer wavelength. On the other hand, when the object is in the vicinity of the vibration center position, the object displaces rapidly and the chopping wave has a shorter wavelength.

In the second embodiment, the turning point is identified by utilizing the wavelength change according to the position of the vibrating plane. When the turning point is identifies according to the wavelength change, there arises a problem as follows. That is, a chopping wave is generated when the vibrating object displaces by $\lambda/2$. If the vibrating object displaces by a distance shorter than $\lambda/2$ and stops before displacing in the opposite direction, the chopping wave cannot have one full amplitude. That is, the vibrating object does not displaces by $\lambda/2$, the chopping waveform is destroyed at the turning point.

Whether this destroyed chopping wave is counted as a wave or not (wavelength is calculated or not) depends on the displacement amount of the vibrating object. Furthermore, in the configuration for calculating a wavelength at the amplitude center position of a chopping wave, if the chopping wave amplitude peak corresponding to the turning point is in the vicinity of the normal chopping wave center position, the high frequency component noise added to the chopping wave affects much. In such a case, a wave is counted with a short wavelength in spite of that the vibrating object has not displaced.

It is also possible to extract a turning point by aiming at a shorter wavelength which can be extracted with stability. However, when a shorter wavelength is taken into consideration, if the vibrating object is overlapped with a plurality of frequency components, the waveform from a first turning point to a second turning point and from the second turning point to the first turning point is not symmetric along the time axis. Consequently, it is impossible to preferably create a vibration data of the object having a plurality of frequency components.

Figure 12:
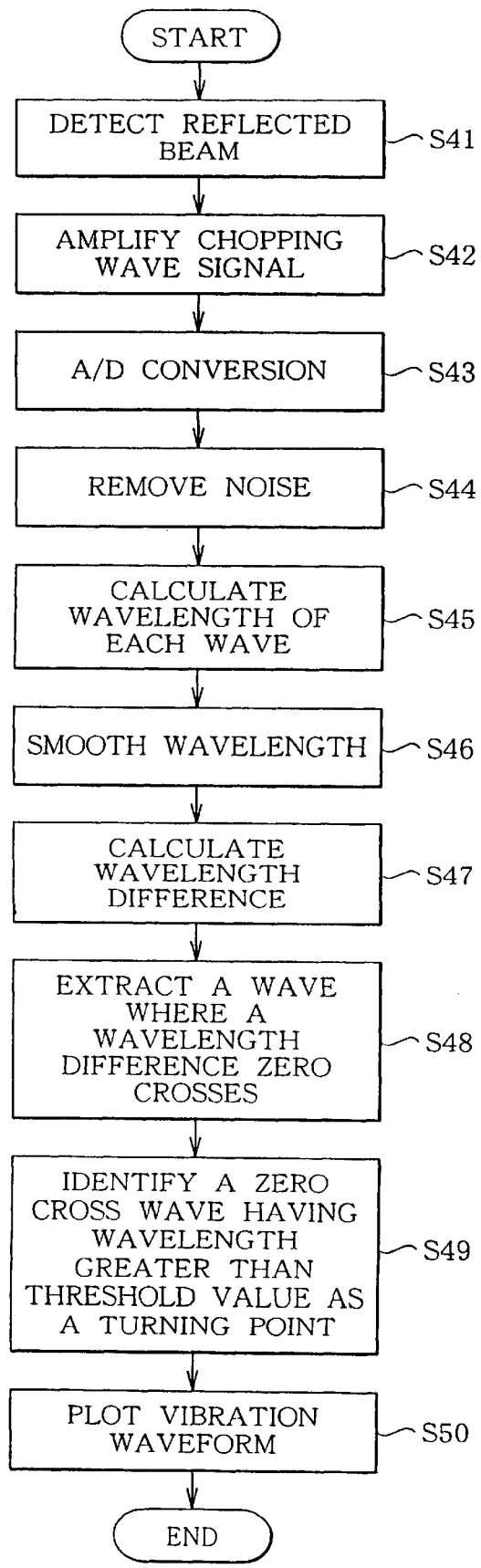
FIG. 12 is a flowchart showing a processing example with the configuration of FIG; 11.

FIG. 12 is a flowchart intending to solve these problems. This flowchart enables to calculate a vibration waveform data of a beat wave (chopping wave) not depending on the behavior of a small chopping wave generated at a turning point, even if a plurality of frequency components are overlapped on the vibration of the object to be measured.

Figure 13:
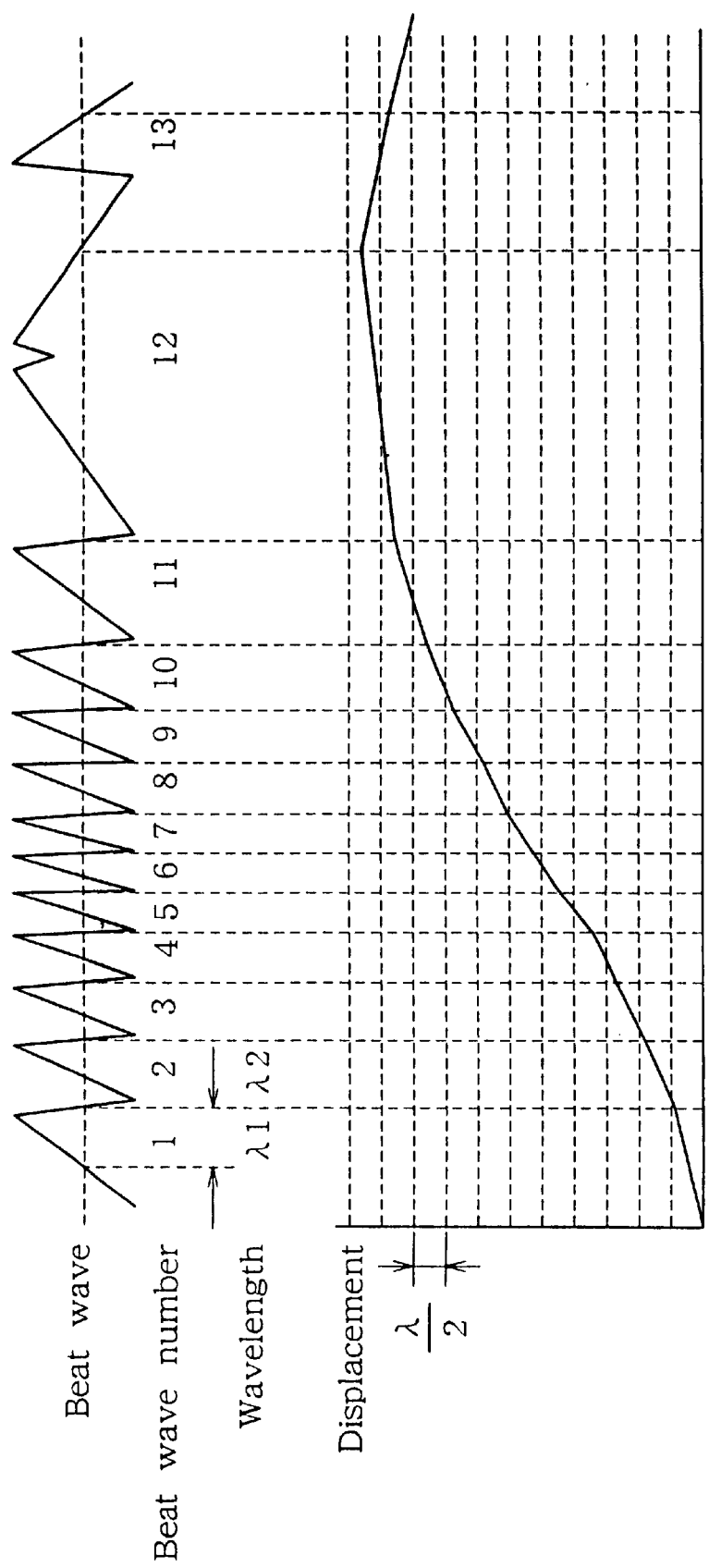
FIG. 13 is a graph showing relationship between the chopping wave data and a vibration waveform used in the flowchart of FIG. 12.

In the example of FIG. 12, firstly, the photo detection unit 2 mixes a reflected beam from the object 1 to be measured, with an oscillated beam in a resonator and the mixed beam is photo-electrically converted (step S42). Furthermore, the signal processing unit 8 amplifies the beat wave (step S42) and convert the amplified beat wave into a digital data (step S43). The calculation unit 6 eliminates a high frequency component of the chopping wave data as a digital data (step S44). FIG. 13 shows an example of a chopping wave data.

Subsequently, the wavelength calculation unit 14A extracts a wavelength data from the chopping wave data (step S45). There are various methods for wavelength calculation. For example, if the chopping wave data is added by a low frequency component, an envelope is generated for the amplitude of the chopping wave data, and the middle point of the envelope is used as a middle line for wavelength calculation. Alternatively, a middle line is generated at the center of amplitude of the chopping wave, so that intersecting points between the middle line and the chopping wave are connected to calculate the wavelength. Furthermore, it is also possible to define a closed region by the envelope and the chopping wave and when the region has a predetermined area or above, the region is counted as a wave for wavelength calculation.

Next, wavelength smoothing is performed (step S46). Accordingly, even if a wavelength is erroneously detected due to a noise added to the chopping wave, this will not affect the turning point identification. That is, vibration is periodic and a wave will not be changed in isolation except for a noise. Consequently, by averaging 5 or 3 preceding and following wavelength values for smoothing, the affect of the wave in isolation can be reduced.

Furthermore, a calculation is performed to obtain a difference between a current wavelength and a preceding current wavelength (step S47, wavelength difference calculation function), so as to decide the wavelength is greater or smaller than the preceding wave. If the wavelength is decreased, the object to be measured is accelerating. On the other hand, if the wavelength is increased, the object decreases its speed. The object slows down its speed and stops at the turning point and then accelerates its speed. Accordingly the point where the speed reduction is changed to speed acceleration is the turning point.

For extracting the point where the speed reduction is changed into speed acceleration, firstly, a zero cross point of a wavelength difference curve (see FIG. 14) is extracted (step S48, zero cross point extraction function). This extracts a point where speed reduction is changed into speed acceleration and a point where the speed acceleration is changed into speed reduction.

Furthermore, among the beat waves containing a zero cross point, the beat wave having a wavelength greater than a predetermined threshold value is determined to be a turning point (step S49, turning point decision function). This identifies a wave which has changed from speed reduction to speed acceleration.

Furthermore, as shown in FIG. 13, according to the turning point and the wavelength, a vibration displacement is plotted, which serves as a vibration waveform data (step S50).

EXAMPLE 1

Next, an example of the second embodiment will be detailed with reference to the attached drawings. In this example, configuration of hardware resources is identical to that of FIG. 3. On the other hand, in this example, the calculation apparatus 14 includes the wavelength calculation unit 14A, the wavelength smoothing unit 14B, and the turning point identification unit 14C shown in FIG. 11. Here, the calculation apparatus 14 is a computer. The computer includes a CPU for performing calculation, a RAM as a main memory, and recording medium containing a program. This recording medium may be any non-volatile medium such as a ROM and magnetic disc.

The recording medium contains various programs, including a vibration measurement program for calculating a vibration waveform data 6a according to the chopping wave data 4Aa. This program is successively executed by the CPU and the computer as the calculation apparatus operates as the aforementioned wavelength calculation unit 14A, the wavelength smoothing unit 14B, and the turning point identification unit 14C.

This vibration measurement program has following instructions to operate the calculation apparatus 14: a wavelength calculation instruction for calculating a wavelength of each chopping wave; wavelength difference calculation instruction for calculating a difference between a current wavelength and a preceding wavelength immediately before; a zero cross point extraction instruction for extracting a point of zero cross of the wavelength curve; and a turning point identification instruction for detecting a wave containing the zero cross point and having a wavelength greater than a predetermined threshold value, and deciding that a turning point of the object to be measured is present at the position of the wave having the greater wavelength than the threshold value. These instructions may be instructions directly causing the CPU to operate and instructions driving an operating system of the calculation apparatus depending on other software. The aforementioned instructions are executed by the calculation apparatus to realize the flowchart of FIG. 12.

Next, the turning point identification processing will be detailed with reference to an example of a specific wave. Here, the turning point identification unit has a threshold value setting function using an average value of a plurality of waves as the threshold value.

Figure 14:
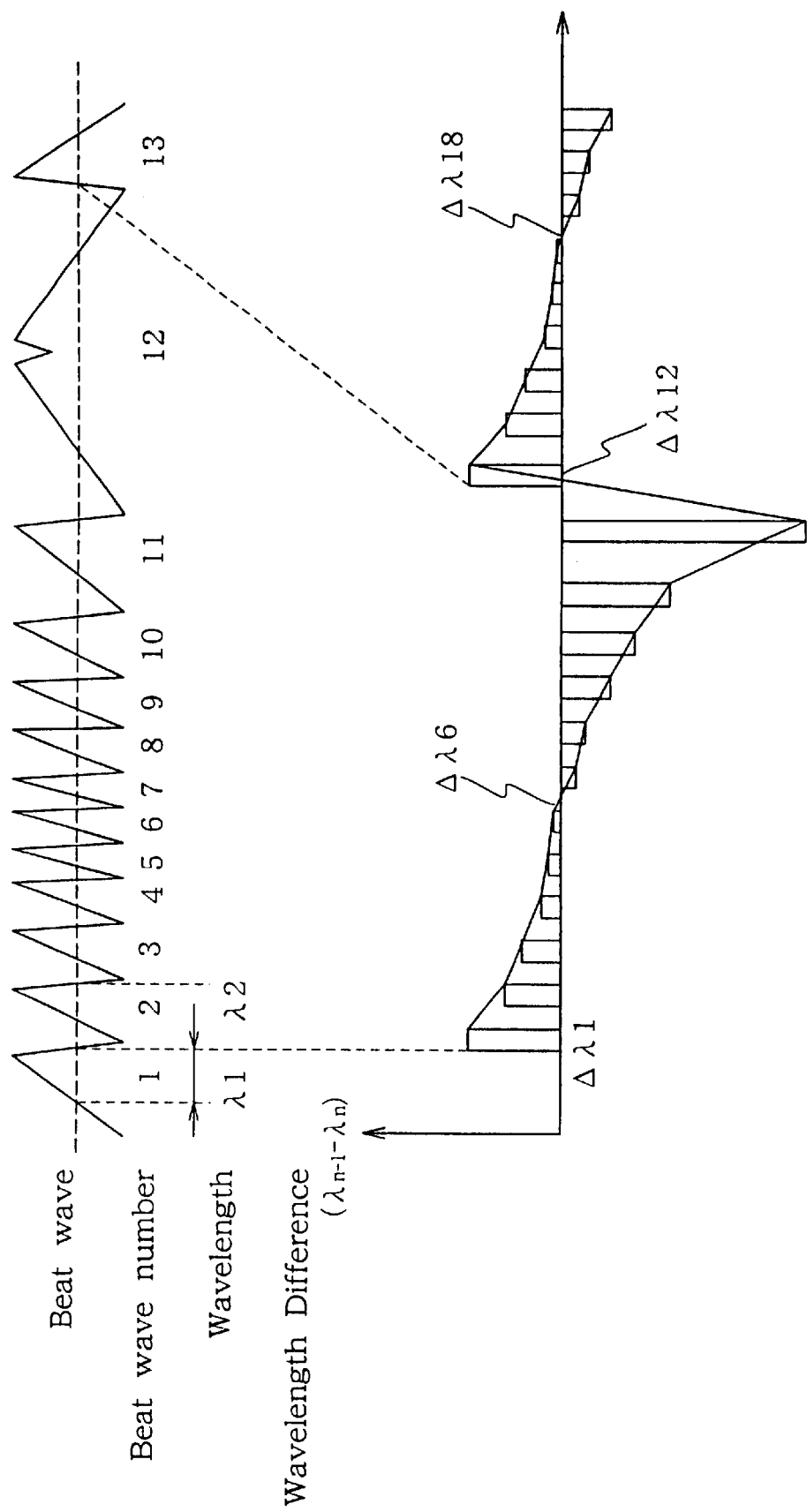
FIG. 14 is a graph showing the relationship between the chopping wave and wavelength difference.

As shown in FIG. 14, firstly, a wavelength of the beat wave is calculated. Here "$\lambda 1$" represents a wavelength of the first beat wave. The wavelength may be calculated from the sampling point number, or from a time interval that the beat wave crosses an arbitrary voltage. Next, increase of the wavelength is calculated. FIG. 14 shows the increase of the current wave from the preceding wave is calculated and aligned along the time axis.

Furthermore, the tops of the wavelength difference are connected to obtain a wavelength curve and calculate the point where the curve crosses the zero line. This zero cross point in FIG. 14 is as follows.

(1) $\Delta\lambda 6$ and $\Delta\lambda 18$ are positions where the beat wave is dense. The beat wavelength becomes shorter and then longer.

(2) $\Delta\lambda 12$ is a position where the beat wave is rare. The beat wavelength becomes longer and then shorter.

The state (2) is the displacement direction change point of the vibrating plane and this point is to be detected.

Figure 15:
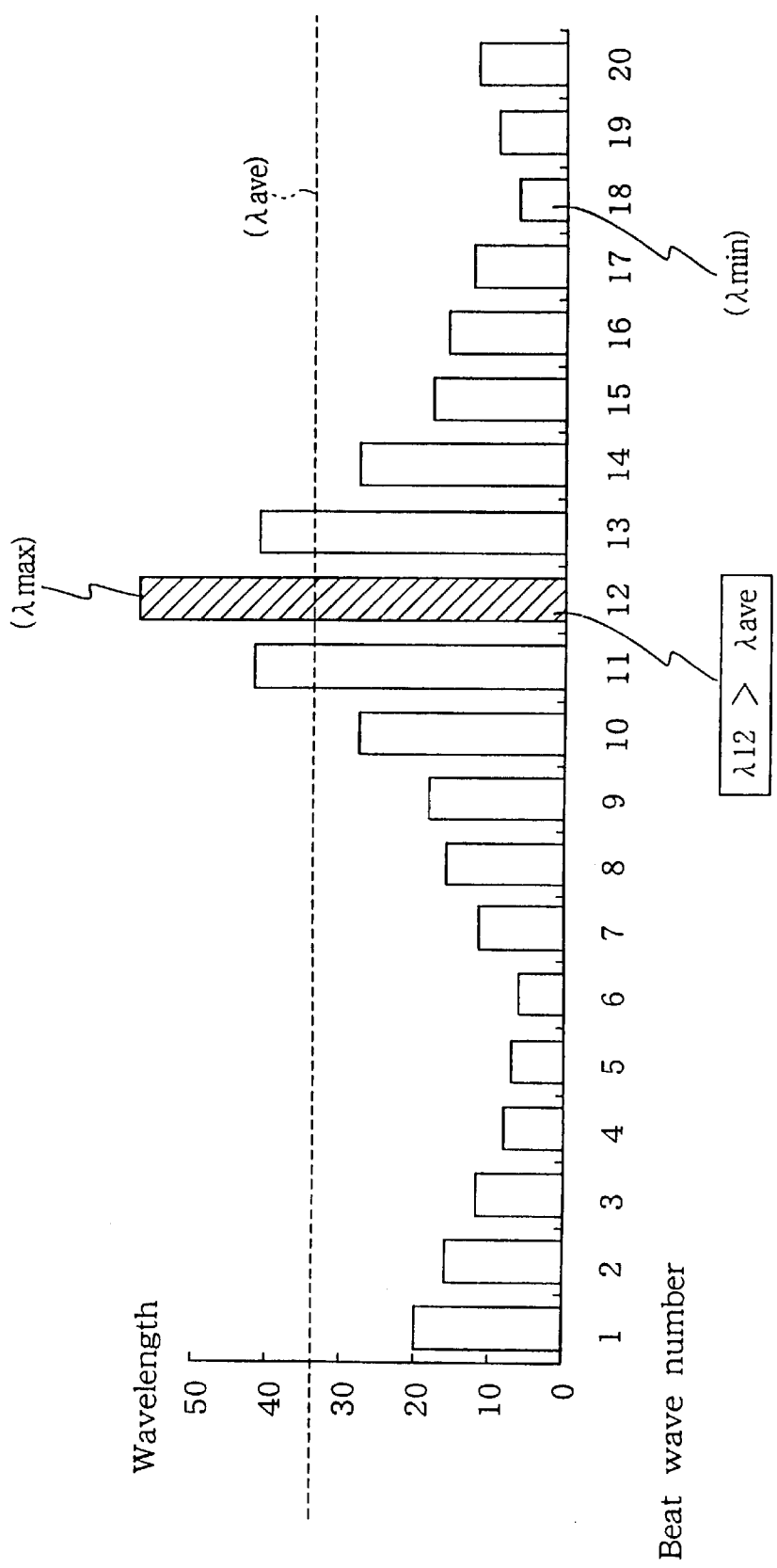
FIG. 15 is a graph showing a wavelength values and an average wavelength value.

For this, a threshold value is defined as follows. As shown in FIG. 15, the maximum wavelength $\lambda\text{max}$ and the minimum wavelength $\lambda\text{min}$ are extracted and their average value $\lambda\text{ave}$ is calculated so as to be used as the threshold value.

Next, according to the threshold value, a beat wave rare portion is detected. The beat wave number is checked at the calculated zero cross point. If the wavelength is greater than the average $\lambda\text{ave}$, the point is determined to be a beat wave rare portion, i.e., displacement direction change point of the vibrating plane.

Thus, the self-mixing vibration measurement apparatus can preferably measure a vibration of an object vibrating with a plurality of frequency components. Furthermore, because the threshold value is an average value, there is no need of changing the threshold value according to the beat wave state. Moreover, the wavelength is smoothed, with the preceding and following wavelength. Among the smoothed wavelength, a wavelength greater than the average value is decided to be the turning point. Accordingly, even if the beat waveform is destroyed in the vicinity of the turning point and a short wavelength occurs in an isolated manner, it is possible to preferably detect a turning point.

Figure 16:
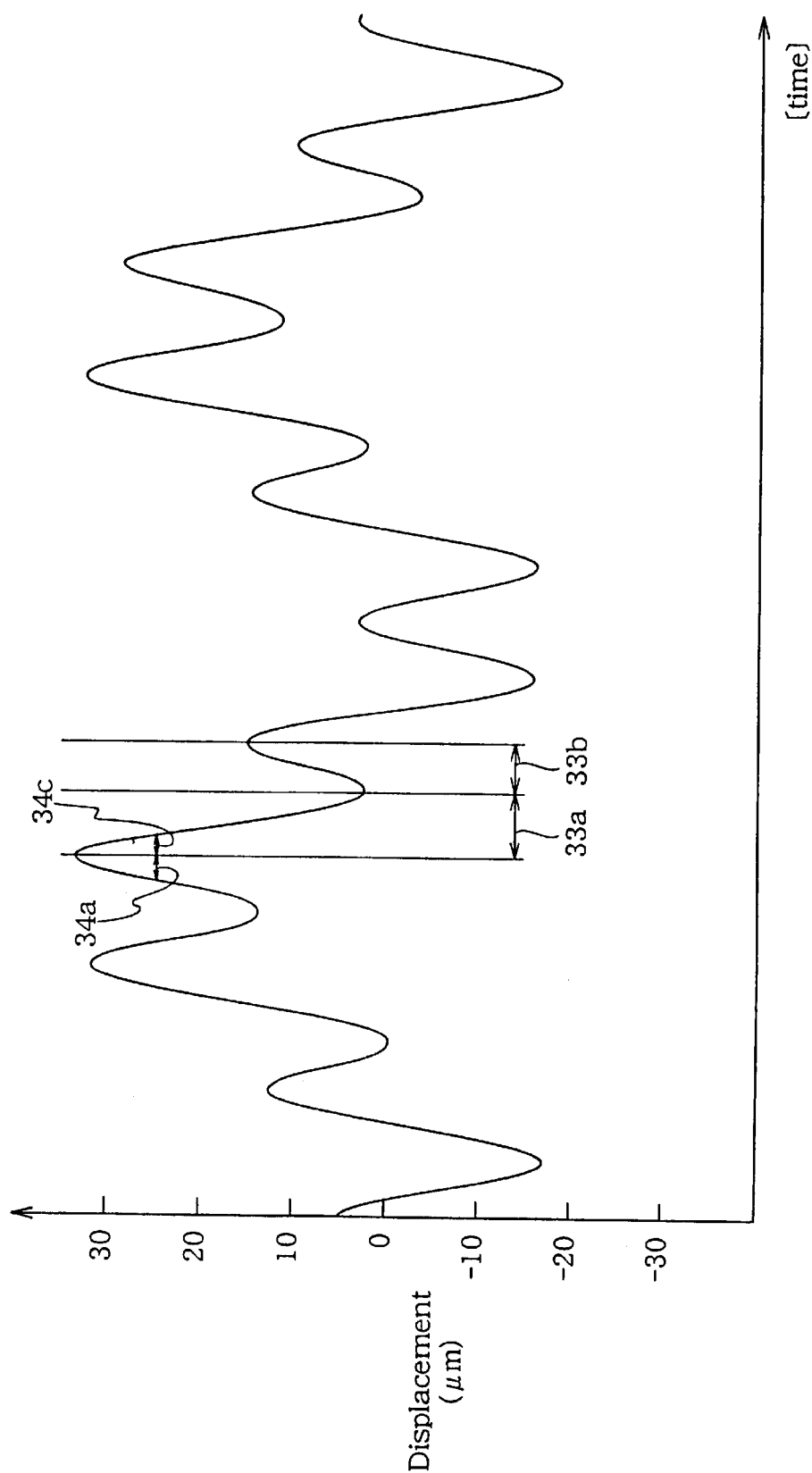
FIG. 16 shows a vibration waveform of an object vibrating with two frequencies mixed.

As has been described above, in this example, the chopping wave wavelength values are compared as a whole and a turning point is identified by a simplified calculation considering only the wavelength values. Accordingly, even if the vibration of the object contains a plurality of frequency components as shown in FIG. 16, it is possible to preferably identify the turning point. Even if the vibration displacement is not cyclic as shown by 33a and 33b, it is possible to preferably identify the turning point.

Thus, according to the present embodiment, in a displacement calculation of simple harmonic motion, it is possible to calculate a turning point even if far from normal distribution. The calculation depends on only the wavelength values, it is possible to calculate a turning point even if a plurality of vibrations are overlapped instead of a chopping wave distribution pattern. Furthermore, the program is rather simple and does not require a large storage capacity or calculation time. Since a laser beam is used to measure vibration of an object, it is possible to perform measurement even if the object is light in weight or at a high temperature unlike an acceleration pickup. That is, the acceleration pickup is a contact type. If the object to be measured is light in weight, the object vibration is changed by weight of the acceleration pickup and if the object is at a high temperature, it is impossible to make contact with the object. The vibration measurement apparatus according to the present embodiment is a non-contact type free from these problems.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. A10-103736 (Filed on Mar. 31, 1998) and No. A10-309019 (Filed on Oct. 29, 1998) including specification, claims, drawings and summary are incorporated herein by reference in its entirety.

What is claimed is:

1. A vibration displacement calculation method utilizing the laser beam Doppler effect to calculate a turning point of a vibrating object, the method comprising:

applying a laser beam oscillated in a laser resonator, to an object to be measured;

mixing an oscillated laser with the laser beam reflected from the vibrating object and outputting a beat wave;

detecting waveform characteristics of each chopping wave in the beat wave; and identifying the turning point of the vibrating object according to a continuous change of the waveform characteristics of the chopping waves.

2. A vibration displacement calculation method as claimed in claim 1, the method further comprising a step of extracting a zero cross point of the continuous change of the chopping waveforms and identifying a turning point of the vibrating object according to the zero cross point.

3. A vibration displacement calculation method as claimed in claim 1, further comprising:

determining a displacement of the vibrating object based on the identified turning point.

4. A vibration displacement calculation method as claimed in claim 3, wherein the identifying of the turning point comprises identifying a turning point using an integral approach for determining the turning point as a point at which that a speed associated with the vibrating object is decreased and the increased.

5. A vibration displacement calculation method as claimed in claim 3, wherein the identifying of the turning point comprises identifying a turning point using a differential approach for determining a change of displacement direction.

6. A vibration measurement apparatus utilizing the laser beam Doppler effect to calculate a turning point of a vibrating object, the apparatus comprising:

a laser resonator for applying an oscillated laser beam to an object to be measured and receiving the return beam reflected from the object;

a beat wave detection unit for detecting a beat wave generated by self-mixing in the laser resonator; and a calculation unit for detecting waveform characteristics for each of the chopping waves in the beat wave and identifying the turning point of the object to be measured, according to a continuous change of the waveform characteristics of the chopping waves.

7. A program product for calculating a turning point of an object to be measured by using a vibration measurement apparatus: comprising a photo detection unit for observing a laser beam reflected from the object; a beat wave detection unit for analyzing a waveform signal output from the photo detection unit and detecting a beat wave; and a calculation unit for signal processing of the beat wave detected; wherein the program causes the calculation unit to:

detect waveform characteristics of each chopping wave in the beat wave; and identify the turning point of the vibrating object according to a continuous change of waveform characteristics of each chopping wave.

8. A vibration displacement calculation method utilizing the laser beam Doppler effect to calculate a turning point of a vibrating object, the method comprising:

applying a laser beam oscillated in a laser resonator, to an object to be measured;

mixing an oscillated laser with the laser beam reflected from the vibrating object and outputting a beat wave;

calculating an ascending inclination and descending inclination of each waveform of the beat wave; and identifying the turning point of the vibrating object according to a change of the ascending and descending inclination values along the time axis.

9. A vibration displacement calculation apparatus configured to determine a vibration displacement by detecting a turning point, said apparatus comprising:

an outputting device for outputting a beat wave as a mixture of an oscillated beam with a laser beam reflected from a vibrating object;

a displacement direction change point device for identifying a displacement direction change point of the vibrating object according to the beat wave; and a turning point determination device for deciding that the displacement direction change point is the turning point.

10. A vibration displacement calculation method for calculating a turning point of an object by utilizing the laser beam Doppler effect, the method comprising:

applying a laser beam oscillated in a laser resonator, to a vibrating object to be measured;

outputting a beat wave as a mixture of the laser beam oscillated and the laser beam reflected from the vibrating object;

generating a differential waveform of the beat wave;

extracting a differential value of a slope waveform as a base of needle peaks that zero-cross twice in a period of time;

detecting a zero-cross point of a longer period than the period of time, on the extracted slope waveform differential value; and deciding that the turning point of the vibrating object is present in the vicinity of the zero cross point of the extracted slope waveform.

11. A vibration displacement calculation method for calculating a turning point of an object by utilizing the laser beam Doppler effect, the method comprising:

applying a laser beam oscillated in a laser resonator, to a vibrating object to be measured;

outputting a beat wave a mixture of the laser beam oscillated and the laser beam reflected from the vibrating object;

generating a differential waveform of the beat wave;

extracting a zero cross point where the differential waveform value becomes zero;

calculating an interval from the zero cross point to the next zero cross point;

averaging continuous three of the zero cross intervals, selecting two zero cross intervals which are greater than the average, and identifying a sign (plus or minus) of the two zero cross intervals; and deciding that the turning point is present in the two intervals if the two intervals have different signs, and that no turning point is present if the signs are identical.

12. A vibration displacement calculation apparatus configured to determine a vibration displacement by detecting a turning point, said apparatus comprising:
- a photo detection unit for observing a laser beam reflected from a vibrating object to be measured;
- a beat wave detection unit for analyzing a waveform signal output from the photo detection unit and detecting a beam wave;
- a differential processing unit for generating a differential waveform for the beat wave;
- a zero cross point extracting unit for extracting a zero cross point where the differential waveform value becomes zero;
- a zero cross interval unit for calculating an interval between the zero cross point extracted by the zero cross extraction unit, and the next zero cross point;
- a differential value sign identification unit for calculating an average of continuous three of zero cross intervals, detecting two continuous intervals greater than the average, and identifying signs (plus or minus) of the two continuous intervals; and
- a decision unit for deciding that the turning point is present in the two intervals if the intervals have different signs and that no turning point is present if the intervals have identical signs.

13. A vibration displacement calculation method for calculating a turning point of a vibrating object to be measured, by utilizing the laser beam Doppler effect, the method comprising:
- applying a laser beam oscillated in a laser resonator, to a vibrating object to be measured;
- mixing the oscillated laser with the laser beam reflected from the vibrating object, so as to output a beat wave;
- calculating a wavelength of a chopping wave in the beat wave; and
- identifying the turning point of the vibrating object according to the calculated wavelength values of chopping waves changing along the time axis.

14. A vibration measurement apparatus comprising:
- a photo detection unit for observing a laser beam reflected from a vibrating object to be measured;
- a beat wave detection unit for analyzing a waveform signal output from the photo detection unit and detecting a beat wave;
- a wavelength calculation unit for calculating wavelength of each beat waves; and
- a turning point identification unit for extracting from a plurality of waves calculated by the wavelength calculation unit, the wave having the longest wavelength and identifying a turning point of the vibrating object displacement direction according to the position of the wave having the longest wavelength.

15. A vibration measurement apparatus as claimed in claim 14, wherein the turning point calculation unit further includes:
- a wavelength difference calculation function for calculating a wavelength difference between tow adjacent waves;
- a zero cross wave extraction function for extracting a wave whose wavelength zero-crosses; and
- a turning point position deciding function for deciding that the turning point of the vibrating object has occurred at the position of the extracted wave having a wavelength greater than a predetermined threshold value.

16. A vibration measurement apparatus as claimed in claim 15, the apparatus further comprising a waveform smoothing unit for smoothing a plurality of waves calculated by the wavelength calculation function.

17. A vibration measurement apparatus as claimed in claim 15, the apparatus further comprising a threshold value setting function, for using an averaged value of wavelengths of the plurality of waves as the threshold value used in the turning point position deciding function.

18. A program product for calculating a vibrating object displacement by using a vibration measurement apparatus configured to determine a vibration displacement by detecting a turning point, said apparatus comprising: a photo detection unit for observing a laser beam reflected from the vibrating object; a beat wave detection unit for analyzing a waveform signal output from the photo detection unit and detecting a beat wave; and a calculation unit for signal processing of the detected beat wave, wherein the program causes the calculation unit to:
- calculate a wavelength for each beat wave;
- calculate a wavelength difference for each two adjacent waves;
- extract a wave having a wavelength which zero crosses; and
- retrieve the extracted zero cross waves to find a wave having a wavelength greater than a predetermined threshold value and decide that the turning point of the vibrating object has occurred at a position of the wave exceeding the threshold value.

19. A vibration displacement calculation apparatus configured to determine a vibration displacement by detecting a turning point, said apparatus comprising:
- an outputting device for outputting a beat wave as a self-mixture of a laser beam oscillated and the laser beam reflected from a vibrating object to be measured;
- a speed reduction identification device for identifying a point where speed reduction is changed into speed acceleration, according to the beat wave; and
- a turning point determination device for deciding that the speed reduction to acceleration point is the turning point of the vibrating object.

* * * * *